United States Patent
Khan et al.

(10) Patent No.: US 8,937,188 B2
(45) Date of Patent: Jan. 20, 2015

(54) PROCESS FOR THE PREPARATION OF LASOFOXIFENE TARTRATE

(75) Inventors: Mubeen Ahmed Khan, Navi Mumbai (IN); Nikhil Rasiklal Trivedi, Navi Mumbai (IN); Nagan Nirmalan Kandasamy, Khidakali (IN); Dayaghan Gangadhar Patil, Kalyan (IN); Vipin Kumar Pandey, Mirzapur (IN); Sukumar Sinha, Navi Mumbai (IN)

(73) Assignee: Glenmark Generics Ltd., Mumbai (IN)

( * ) Notice: Subject to any disclaimer, the term of this patent is extended or adjusted under 35 U.S.C. 154(b) by 492 days.

(21) Appl. No.: 13/265,854

(22) PCT Filed: Apr. 27, 2010

(86) PCT No.: PCT/IN2010/000266
§ 371 (c)(1), (2), (4) Date: Oct. 21, 2011

(87) PCT Pub. No.: WO2010/125578
PCT Pub. Date: Nov. 4, 2010

(65) Prior Publication Data
US 2012/0045648 A1    Feb. 23, 2012

(30) Foreign Application Priority Data

Apr. 29, 2009  (IN) .......................... 1138/MUM/2009
Jul. 15, 2009   (IN) .......................... 1648/MUM/2009

(51) Int. Cl.
  *C07D 207/04*  (2006.01)
  *C07D 207/08*  (2006.01)
(52) U.S. Cl.
  CPC ................................... *C07D 207/08* (2013.01)
  USPC ......................................................... 548/576
(58) Field of Classification Search
  None
  See application file for complete search history.

(56) References Cited

U.S. PATENT DOCUMENTS

| 5,948,809 A | 9/1999 | Chiu et al. |
| 6,608,212 B1 | 8/2003 | Miller |
| RE39,558 E | 4/2007 | Cameron et al. |

FOREIGN PATENT DOCUMENTS

WO        9621656 A1    7/1996

*Primary Examiner* — Michael Barker
(74) *Attorney, Agent, or Firm* — H. Carmen & Associates PLLC

(57) ABSTRACT

A solid crystalline form of 1-(2-[4-(6-methoxy-3,4-dihydronaphthalene-1-y) phenoxy]ethyl)pyrrolidine, and a preparing process thereof are provided. The aforesaid compound is a key intermediate in the synthesis of lasofoxifene. A process for preparing lasofoxifene, a process for purifying lasofoxifene tartrate, and a crystalline form of lasofoxifene tartrate are also provided.

16 Claims, 9 Drawing Sheets

PROCESS FOR THE PREPARATION OF LASOFOXIFENE TARTRATE

PRIORITY

This application is a 35 U.S.C. 371 National Stage Filing of International Application No. PCT/IN2010/000266, filed Oct. 27, 2008, which claims priority under 35U.S.C. 119 (a-d) to Indian Provisional Applications 1138/MUM/2009, filed on Apr. 29, 2009, and 1648/MUM/2009 filed on Jul. 15, 2009, the contents of which are incorporated by reference herein.

FIELD OF INVENTION

The present invention relates to solid state chemistry of 1-(2-[4-(6-methoxy-3,4-dihydronaphthalene-1-yl)phenoxy] ethyl)pyrrolidine, a process for its preparation and its use as an intermediate in the synthesis of lasofoxifene.

BACKGROUND OF THE INVENTION 1-(2-[4-(6-methoxy-3,4-dihydronaphthalene-1-yl)phenoxy]ethyl)pyrrolidine, as shown below,

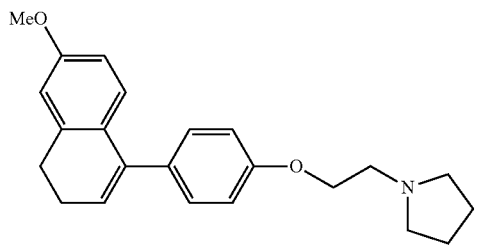

Formula IV is a key intermediate in the preparation of lasofoxifene and its salts. Lasofoxifene D-tartrate, (−)-(5R,6S)-6-Phenyl-5-[4-[2-(1-pyrrolidinyl)ethoxy]phenyl]-5,6,7,8tetrahydronaphthalen-2-ol D tartrate, represented by the structural formula,

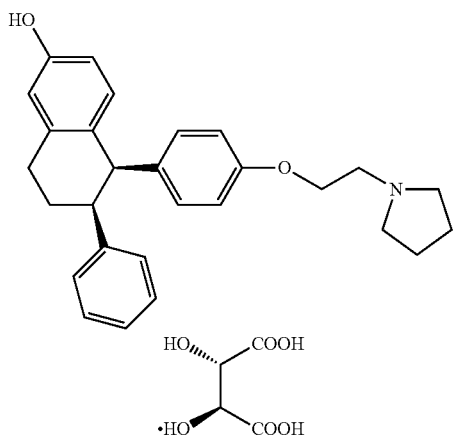

is an estrogen agonist. FABLYN® (lasofoxifene) functions as selective estrogen receptor modulator (SERM) for the treatment of osteoporosis in post-menopausal women at increased risk of fracture and has received approval from the European Commission (EC). FABLYN® was submitted for approval in Europe in January 2008.

Lasofoxifene is disclosed in U.S. Pat. No. RE39,558 while its tartrate salt is disclosed in U.S. Pat. Nos. 5,948,809. RE39,558 describes a process of preparing 1-(2-[4-(6-Methoxy-3,4-dihydronaphthalene-1-yl)phenoxy]ethyl)pyrrolidine, which is obtained as an oil, by the reaction of 1-[2-(4-bromophenoxy)ethyl)]pyrrolidine and 6-methoxy-1-tetralone with butyl lithium (BuLi) in tetrahydrofuran (THF) and in the presence of cesium chloride.

Polymorphic forms occur where the same composition of matter crystallizes in a different lattice arrangement resulting in, for example, different thermodynamic properties and stabilities specific to the particular polymorph form. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks.

When a compound is in its solid form, it allows ease of handling particularly when said compound participates in a multiple step synthesis. Herein, the preparation and isolation of 1-(2-[4-(6-methoxy-3,4-dihydronaphthalene-1-yl)phenoxy]ethyl)pyrrolidine in its solid and crystalline state subsequently contributes to the facile synthesis of lasofoxifene.

SUMMARY OF THE INVENTION

The present invention relates to 1-(2-[4-(6-methoxy-3,4-dihydronaphthalene-1-yl)phenoxy]ethyl)pyrrolidine in solid form.

The present invention relates to 1-(2-[4-(6-methoxy-3,4-dihydronaphthalene-1-yl)phenoxy]ethyl)pyrrolidine in a solid crystalline state characterized by atleast one of below:

(i) XRD peaks at 9.13, 10.5, 15.78, 17.04, 18.06, 18.37, 19.01, 21.01, 21.13, 21.86, 22.87 and 23.43±0.2 °2Theta (ii) IR peaks at 554.9, 602, 622.7, 648, 674, 747.7, 790.8, 809.9, 817.1, 845.1, 79.7, 905.3, 953, 974, 1046, 1119.2, 1162.9, 1152, 1175.7, 1204.4, 1249.5, 1280.5, 1303, 1330, 1356.6, 1374.3, 1556, 1455.7, 1491.1, 1508.4, 1566.5, 1608.4, 1751.2, 1881.5, 2080.4, 2773.4, 2809.9, 2920.4, 2940.5, 3031.9, 3444.4 cm$^{-1}$ (iii) DSC onset of 71.17° C.±2.0° C. and endset of 74.35° C.±2.0° C.

(iv) $^1$H NMR (400 MHz, CDCl$_3$): §7.26-7.23 (d, J=10.4 H/z, 2H), 6.96-6.90 (t, 3H), 6.76 (s, 1H), 6.64-6.62 (d, 11.2 Hz, 1H), 5.92-5.89 (t, 1H) 4.16-4.12 (t, 2H), 3.78 (s, 3H) 2.94-2.90 (t, 2H), 2.83-2.78 (t, 2H), 2.64 (s, 4H), 2.39-2.32 (m, 2H) 1.81 (s, 4H) m/z=350 (M+H): melting point range between 71° C. and 75° C.

The aforementioned characteristics are substantially in accordance with FIGS. 1 to 4.

The present invention provides a process for the preparation of a solid crystalline form of 1-(2-[4-(6-methoxy-3,4-dihydronaphthalene-1-yl)phenoxy]ethyl)pyrrolidine, a compound of formula IV, comprising reacting 6-methoxy-1-tetralone with Grignard reagent of 1-[2-(4-bromophenoxy) ethyl)]pyrrolidine, a compound of formula III

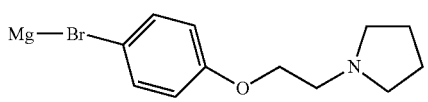

Formula III in the presence of a solvent.

The present invention provides a process for the preparation of 1-(2-[4-(6-methoxy-3,4-dihydronaphthalene-1-yl)phenoxy]ethyl)pyrrolidine, a compound of formula IV, Formula IV

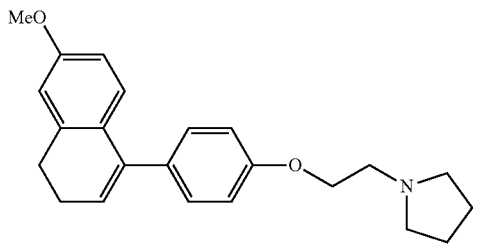

comprising:
a) reacting a compound of formula II with Mg to form a Grignard reagent of formula III Formula II

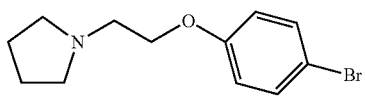

Formula III

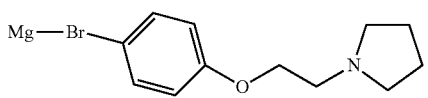

b) reacting the compound of formula III with 6-methoxy-1-tetralone in the presence of a solvent to obtain a crystalline solid 1-(2-[4-(6-methoxy-3,4 dihydronaphtalene-1-yl)phenoxy]ethyl)pyrrolidine, a compound of formula IV.

The present invention provides a process for the preparation of, Cis-6-phenyl-5-[4-(2-pyrrolidin-1-yl-ethoxy)phenyl]-5,6,7,8-tetrahydronaphthalene-2-ol), compound of formula I, Formula I

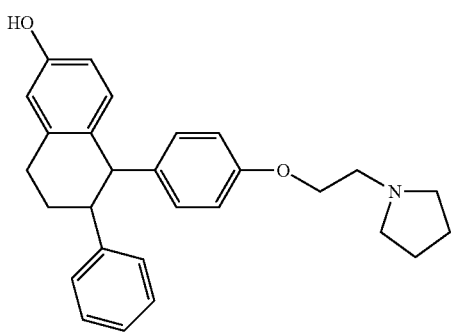

comprising:
a) halogenating solid 1-(2-[4-(6-methoxy-3,4 dihydronaphthalene-1-yl)phenoxy]ethyl)pyrrolidine, a compound of formula IV, Formula IV

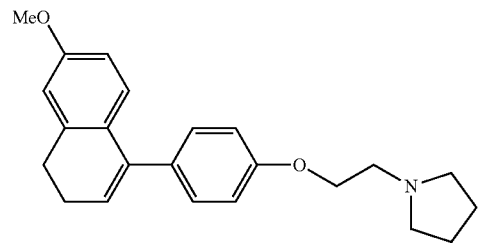

to obtain a compound of formula V,

Formula V

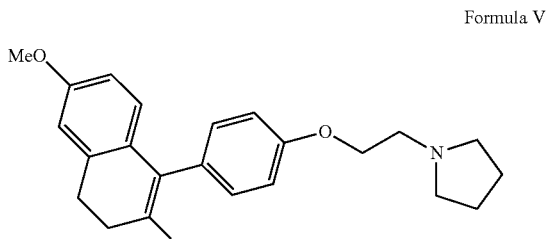

where X is a halogen selected from chlorine, bromine, iodine.
c) phenylating the compound of formula V to obtain 1-(2-[4-(6-Methoxy-2-phenyl-3,4-dihydronaphthalene-1-yl)phenoxy]ethyl)pyrrolidine hydrochloride a compound of formula VI, Formula VI

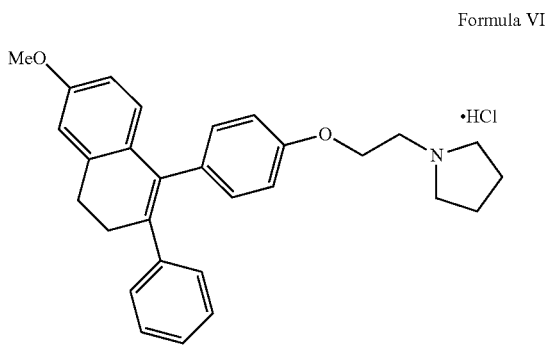 [SMILES: COc1ccc2c(c1)CCC(c1ccccc1)=C2c1ccc(OCCN2CCCC2)cc1 ; Cl]

wherein the phenylating reagent is selected from phenyl boronic acid, phenyl boronic acid glycol ester, phenyl boron dihalogen like phenyl boron dichloride, phenyl boron dibromide and phenyl boron diiodide.
d) reducing the compound of formula VI to obtain Cis-1-(2-[4-(6-Methoxy-2-phenyl-1,2,3,4-tetrahydronaphthalene-1-yl)phenoxy]ethyl)pyrrolidine, a compound of formula VII, Formula VII

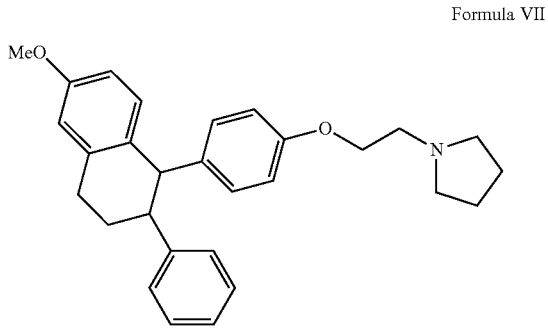 [SMILES: COc1ccc2c(c1)CCC(c1ccccc1)C2c1ccc(OCCN2CCCC2)cc1]

wherein the reducing agent is selected from (5-20%) palladium/C (Pd/C), palladium hydroxide, Raney Ni and activated alloy catalyst;

e) reacting the compound of formula VII with an acid to form cis-6-phenyl-5-[4-(2-pyrrolidin-1-yl-ethoxy)phenyl]-5,6,7,8-tetrahydronaphthalene-2-ol), a compound of formula I

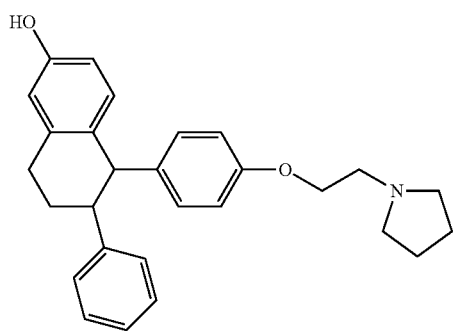

Formula I wherein the acid is selected from 48% hydrobromic acid, hydroiodic acid, acetic acid in hydrobromic acid and boron tribromide in methylene chloride.

f) optionally converting the compound of formula I to its corresponding pharmaceutically acceptable salt/s.

The present invention provides a process for purification of lasofoxifene tartrate comprising:
a) providing a solution of lasofoxifene tartrate in a solvent or a mixture of solvents or their aqueous mixtures ;
b) precipitating the solid from the solution, and
c) isolating lasofoxifene tartrate.

The present invention provides crystalline lasofoxifene tartrate characterized by an X-ray Diffraction (XRD) spectrum, which is substantially in accordance with FIG. 5 and a Differential Scanning calorimetric (DSC) thermogram, which is substantially in accordance with FIG. 6.

The present invention provides crystalline lasofoxifene tartrate further characterized by Infrared (IR) spectrograph, which is substantially in accordance with FIG. 7; and a Thermogravimetric Analysis (TGA) thermogram, which is substantially in accordance with FIG. 8.

The present invention provides crystalline lasofoxifene tartrate further characterized by crystalline particles with a specific surface area from about 4 $m^2/g$ to about 7 $m^2/g$, as measured by Brunauer-Emmett-Teller (BET) method.

The present invention provides crystalline lasofoxifene tartrate particles, wherein 90% of the particles have a particle size less than 750 μm.

The present invention provides crystalline lasofoxifene tartrate having a flake morphology as observed by SEM, which is substantially in accordance with FIG. 9.

The present invention provides crystalline lasofoxifene tartrate having tapped bulk density ranging from about 0.26 g/ml to about 0.56 g/ml and untapped bulk density ranging from about 0.22 g/ml to about 0.52 g/ml.

DETAILED DESCRIPTION OF INVENTION

The present invention relates to solid state chemistry of 1-(2-[4-(6-methoxy-3,4-dihydronaphthalene-1-yl)phenoxy]ethyl)pyrrolidine, a compound which may be a useful intermediate for preparing lasofoxifene.

The present invention relates to solid crystalline 1-(2-[4-(6-methoxy-3,4-dihydronaphthalene-1-yl)phenoxy]ethyl)pyrrolidine, a compound of formula IV,

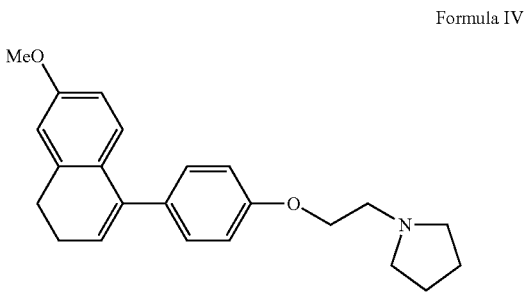 [SMILES: COc1ccc2c(c1)CCC=C2c1ccc(OCCN2CCCC2)cc1]

Figure 1:
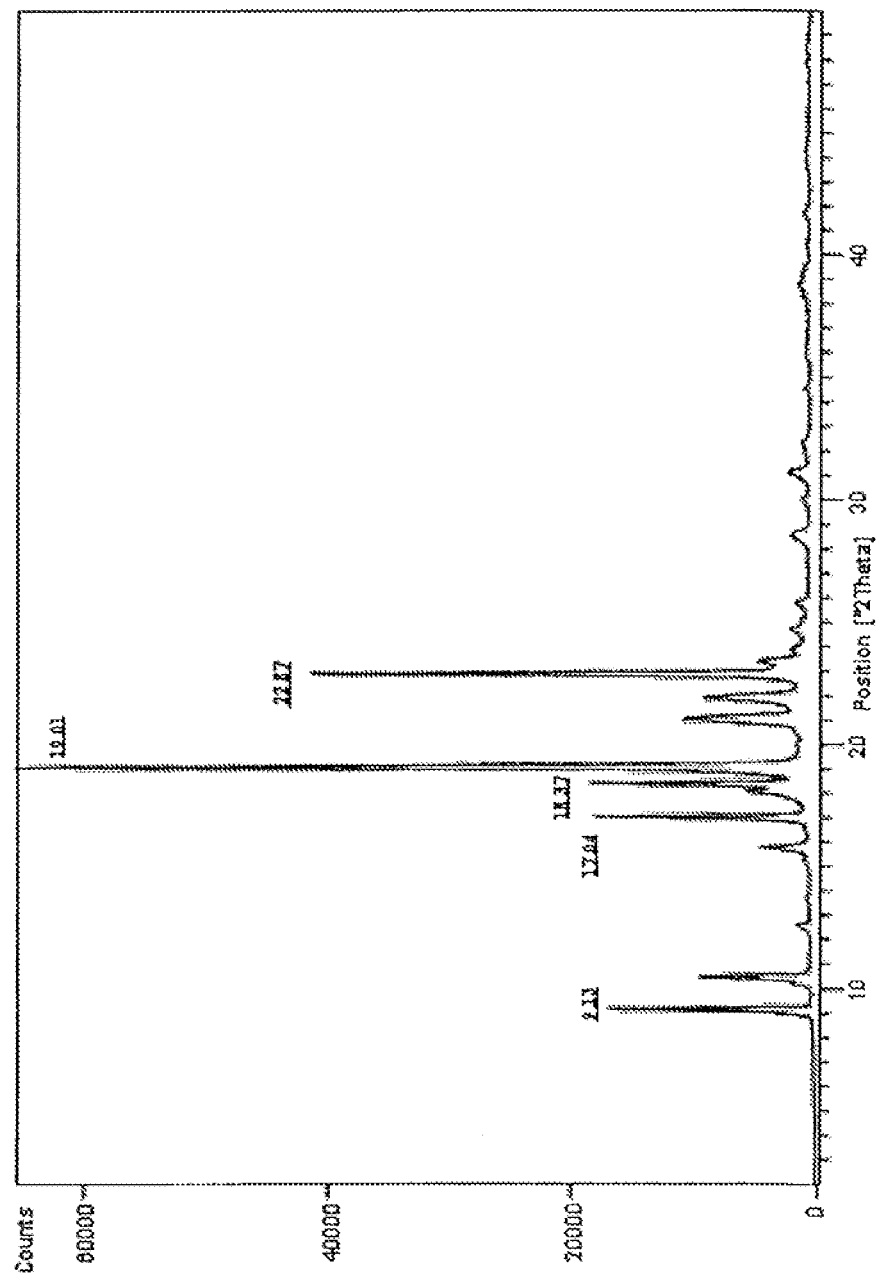
FIG. 1 represents an XRD diffractogram of 1-(2-[4-(6-methoxy-3,4-dihydronaphthalene-1-yl)phenoxy]ethyl)pyrrolidine obtained from example 1

Formula IV characterized by XRD peaks at 9.13, 10.5, 15.78, 17.04, 18.06, 18.37, 19.01, 21.01, 21.13, 21.86, 22.87 and 23.43± 0.2 °2 theta, which is substantially in accordance with FIG. 1.

X-Ray Powder were performed on ARL X-Ray Diffractometer model XPERT-PRO (PANalytical) scanning parameters start position [° 2Th.] 2.01 and End position [° 2Th.] 49.98.

Figure 3:
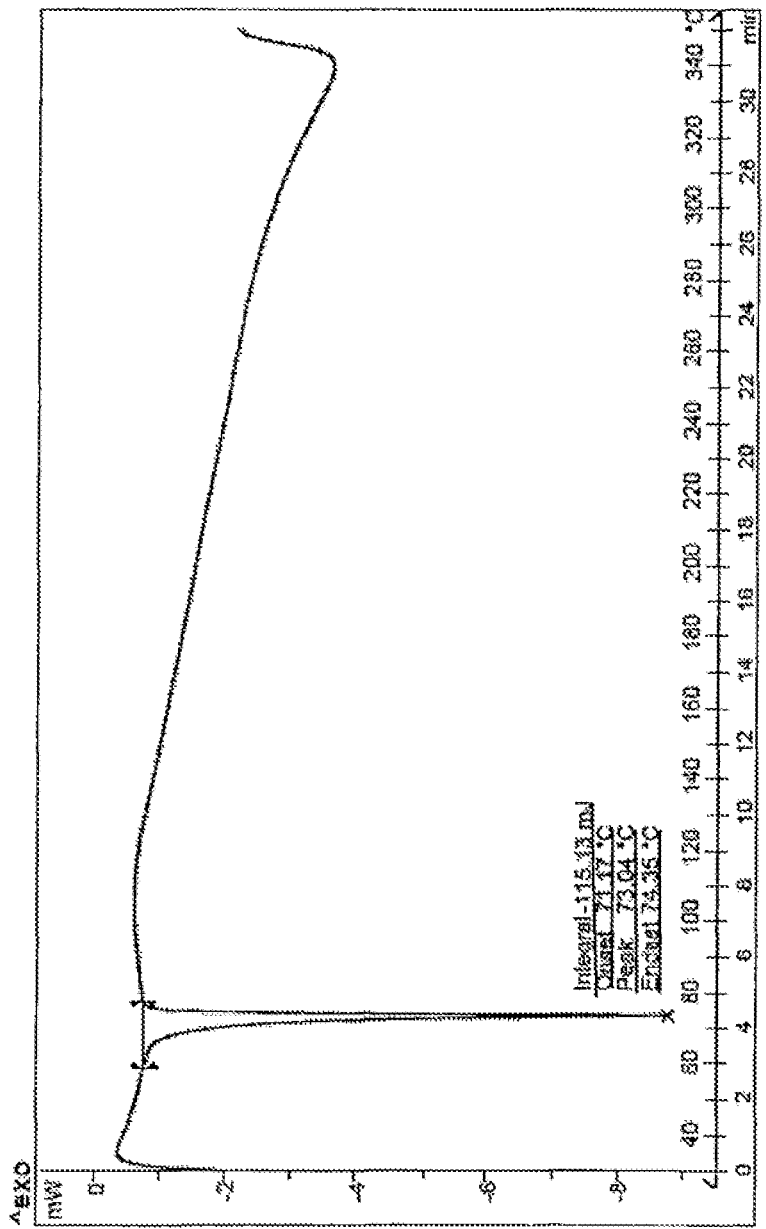
FIG. 3 represents a DSC thermogram of 1-(2-[4-(6-methoxy-3,4-dihydronaphthalene-1-yl)phenoxy]ethyl)pyrrolidine obtained from example 1

The compound of formula IV is characterized by a DSC with endothermic curve at about 73.04° C. and onset of 71.17° C.±2.0° C. and endset of 74.35° C.±2.0° C., which is substantially in accordance with FIG. 3, is measured by a Differential Scanning calorimeter (DSC 822, Mettler Toledo) at a scan rate of 10° C. per minute with an Indium standard.

Figure 2:
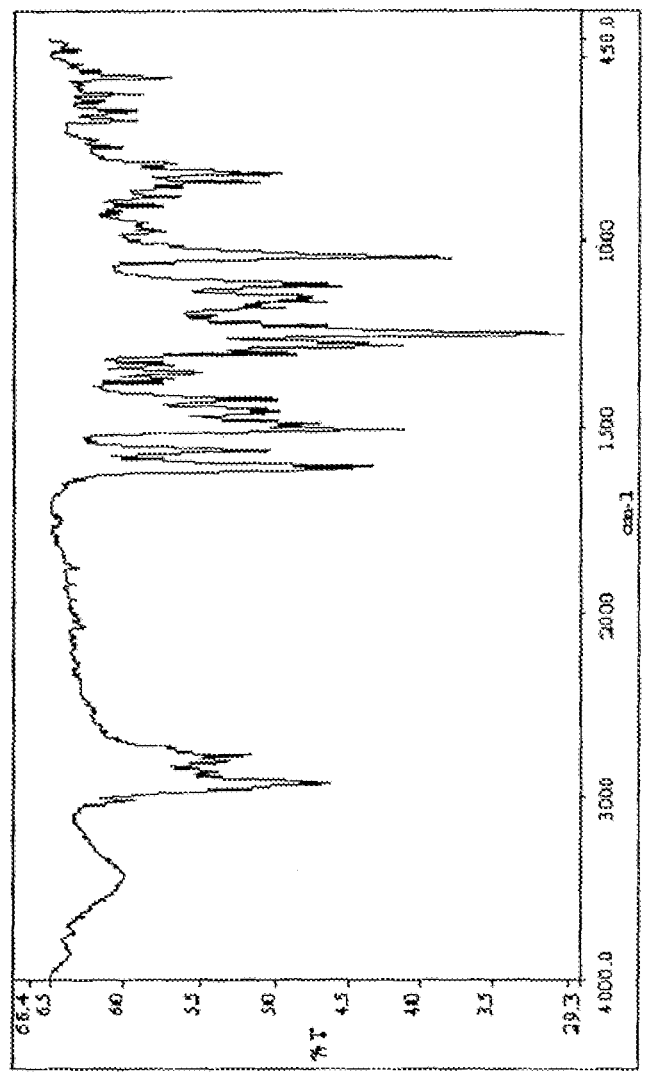
FIG. 2 represents an IR spectra of 1-(2-[4-(6-methoxy-3,4-dihydronaphthalene-1-yl)phenoxy]ethyl)pyrrolidine obtained from example 1

The compound of formula IV is also characterized by IR peaks at 554.9, 602, 622.7, 648, 674, 747.7, 790.8, 809.9, 817.1, 845.1, 879.7, 905.3, 953, 974, 1046, 1119.2, 1162.9, 1152, 1175.7, 1204.4, 1249.5, 1280.5, 1303, 1330, 1356.6, 1374.3, 1556, 1455.7, 1491.1, 1508.4, 1566.5, 1608.4, 1751.2, 1881.5, 2080.4, 2773.4, 2809.9, 2920.4, 2940.5, 3031.9, 3444.4 $cm^{-1}$, which is substantially in accordance with FIG. 2.

Figure 4:
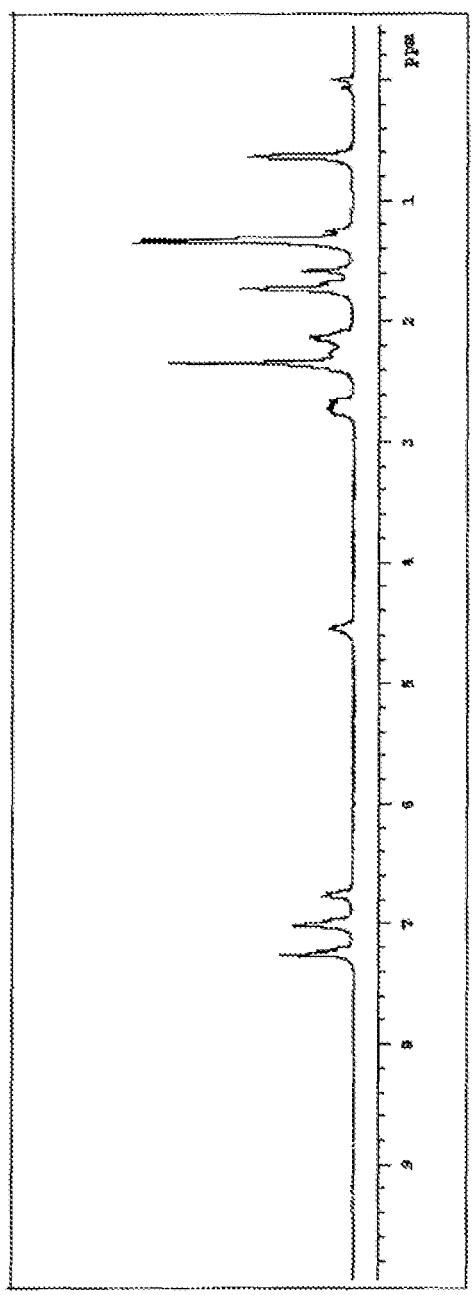
FIG. 4 represents an NMR spectra of 1-(2-[4-(6-methoxy-3,4-dihydronaphthalene-1-yl)phenoxy]ethyl)pyrrolidine obtained from example 1

The compound of formula IV exhibits an $^1$H NMR (400 MHz, $CDCl_3$): §7.26-7.23 (d, J=10.4 H/z, 2H), 6.96-6.90 (t, 3H), 6.76 (s, 1H), 6.64-6.62 (d, 11.2 Hz, 1H), 5.92-5.89 (t, 1H), 4.16-4.12 (t, 2H), 3.78 (s, 3H) 2.94-2.90 (t, 2H), 2.83-2.78 (t, 2H), 2.64 (s, 4H), 2.39-2.32 (m, 2H) 1.81 (s, 4H);

m/z=350 (M+H): melting point range between 71° C. and 75° C., which is substantially in accordance with FIG. 4.

The present invention provides a process for the preparation of 1-(2-[4-(6-Methoxy-3,4-dihydronaphthalene-1-yl) phenoxy]ethyl)pyrrolidine comprising reacting 6-methoxy-1-tetralone with a Grignard reagent.

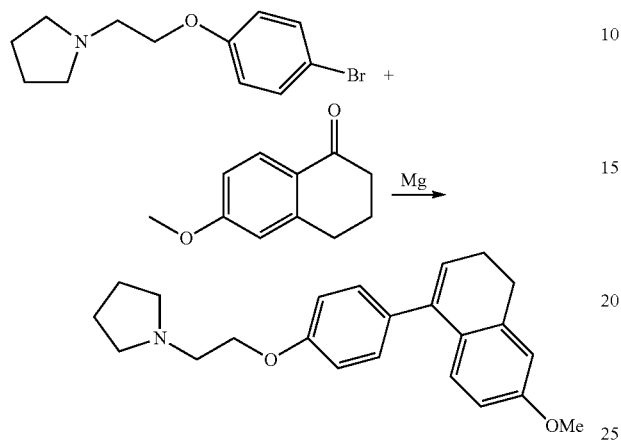

The process above further comprises adding 6-methoxy-1-tetralone in the desired solvent to a Grignard reagent. The Grignard reagent is prepared by reacting 1-[2-(4-bromophenoxy)ethyl)]pyrrolidine with Mg metal in a solvent.

The solvents for carrying out the reaction are selected from ether solvents such as tetrahydrofuran, diethyl ether and diisopropyl ether. Preferably the solvent is tetrahydrofuran (THF).

The reaction is carried out at about room temperature and the reaction time can vary from between about 12 hours to about 20 hours. Preferably, the reaction transpires between about 14 hours to about 16 hours. Once the reaction is completed, water is added to the reaction mass and filtered. The filtrate is acidified.

The extraneous materials or impurities were removed by extraction and the aqueous layer is basified.

The product from the basic solution is extracted by a solvent and the solvent is concentrated. The residue obtained is taken up in diisopropyl ether and stirred for about 30 min to about 10 hours. Preferably for about 4 hours to about 6 hours, whereby 1-(2-[4-(6-methoxy-3,4-dihydronaphthalene-1-yl) phenoxy]ethyl)pyrrolidine is obtained as a crystalline solid having a melting range between 71° C. to 75° C.

The compound of formula II, 1-(2-[4-bromophenoxy) ethyl)]pyrrolidine, can be made by any method known in the art. Illustratively, it is described in U.S. Pat. No. 3,321,483, which is included by reference herein, in its entirety.

Further, the present invention provides the conversion of the solid crystalline 1-(2-[4-(6-Methoxy-3,4-dihydronaphthalene-1-yl)phenoxy]ethyl)pyrrolidine to lasofoxifene by processes known in the art. Illustratively, it is described in U.S. Pat. No. RE39,558, which is included by reference herein, in its entirety.

The present invention provides a process for the preparation of cis-6-phenyl-5-[4-(2-pyrrolidin-1-yl-ethoxy)phenyl]-5,6,7,8-tetrahydronaphthalene-2-ol), a compound of formula I, Formula I

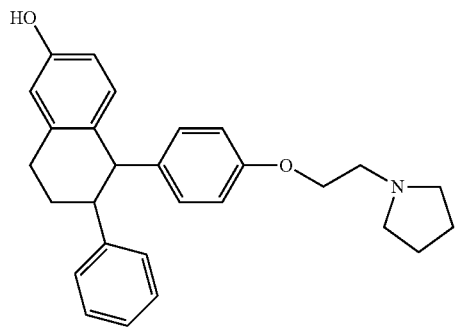

comprising:
a) halogenating solid 1-(2-[4-(6-Methoxy-3,4-dihydronaphthalene-1-yl)phenoxy]ethyl)pyrrolidine a compound of formula IV, compound of formula IV, Formula IV

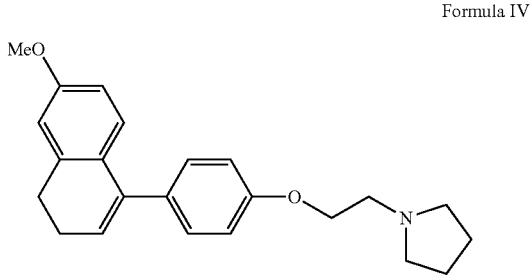 [SMILES: COc1ccc2c(c1)CCC=C2c1ccc(OCCN2CCCC2)cc1]

to obtain a compound of formula V,

Formula V

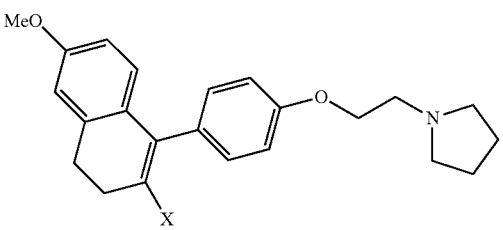

where X is a halogen selected from chlorine, bromine, iodine;
b) phenylating the compound of formula V to obtain 1-(2-[4-(6-Methoxy-2-phenyl-3,4-dihydronaphthalene-1-yl)phenoxy]ethyl)pyrrolidine hydrochloride, a compound of formula VI, Formula VI

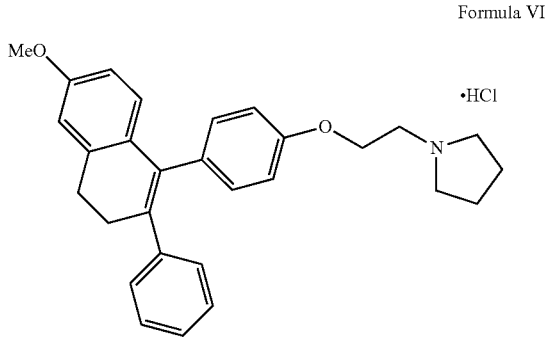 [SMILES: COc1ccc2c(c1)CCC(c1ccccc1)=C2c1ccc(OCCN2CCCC2)cc1 ; Cl]

wherein the phenylating reagent is selected from phenyl boronic acid, phenyl boronic acid glycol ester, phenyl boron di-halogen like phenyl boron dichloride, phenyl boron dibromide and phenyl boron diiodide. Preferably the phenylating reagent is phenyl boronic acid;

c) reducing the compound of formula VI to obtain cis-1-(2-[4-(6-Methoxy-2-phenyl-1,2,3,4-tetrahydronaphthalene-1-yl)phenoxy]ethyl)pyrrolidine, a compound of formula VII, Formula VII

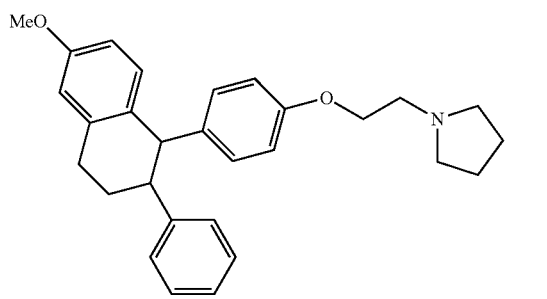

wherein the reducing agent is selected from (5-20%) palladium/C, palladium hydroxide, Raney Nickel and activated alloy catalyst. Preferably the reducing agent is (20%) palladium/C.

d) reacting the compound of formula VII with an acid to form cis-6-phenyl-5-[4-(2-pyrrolidin-1-yl-ethoxy)phenyl]-5,6,7,8-tetrahydronaphthalene-2-ol, a compound of formula I Formula I

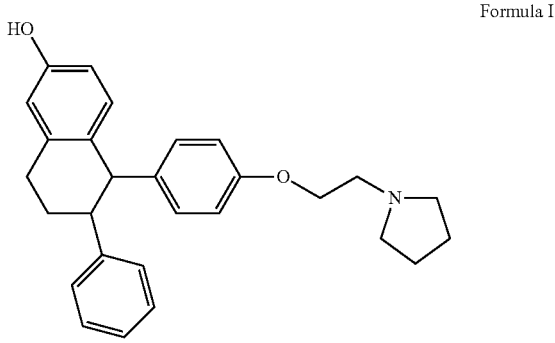 [SMILES: Oc1ccc2c(c1)CCC(c1ccccc1)C2c1ccc(OCCN2CCCC2)cc1]

wherein the acid is selected from 48% hydrobromic acid, hydroiodic acid, acetic acid in hydrobromic acid and boron tribromide in methylene chloride. Preferably the acid is 48% hydrobromic acid;

e) optionally, converting the compound of formula I to its corresponding pharmaceutically acceptable salt/s.

In a) of the process above, the halogenating agent is selected from calcium hypochlorite, chlorine, bromine, aqueous chlorine solutions, aqueous bromine solutions, N-chlorosuccinimide, sodium hypobromite, pyridinium bromide perbromide, N-bromosuccinimide, and chloramine T. Preferably the halogenating agent is pyridinium bromide perbromide.

The solvents for carrying out the reaction are selected from C1-CC4 alcohol such as methanol, ethanol, isopropanol; ether solvents such as tetrahydrofuran, diethyl ether and diisopropyl ether. Preferably the solvent is tetrahydrofuran (THF).

In b) of the process above phenylation is carried out using suitable phenylating agent selected from phenyl boronic acid, phenyl boronic acid glycol ester, phenyl boron di-halogen like phenyl boron dichloride, phenyl boron dibromide and phenyl boron diiodide. Preferably the phenylating reagent is phenyl boronic acid;

The solvents for carrying out the reaction are selected from water, ether solvents such as tetrahydrofuran, diethyl ether and diisopropyl ether and mixtures thereof. Preferably the solvent is a mixture of water and tetrahydrofuran (THF).

The reaction can be carried out at a temperature ranging from 20° C. to reflux temperature of the solvent. Preferably, the reaction transpires at the reflux temperature of the solvents.

In c) of the above process reduction is carried out using reducing agent selected from (5-20%) palladium/C, palladium hydroxide, Raney Nickel and activated alloy catalyst. Preferably the reducing agent is (20%) palladium/C.

The reduction is carried out by hydrogenating at a pressure of about 120 psi to 200 psi. Preferably the hydrogenation pressure is 150 psi.

In d) of the above process compound of formula VII is converted to compound of formula I by treating with an acid selected from 48% hydrobromic acid, hydroiodic acid, acetic acid in hydrobromic acid and boron tribromide in methylene chloride. Preferably the acid is 48% hydrobromic acid.

The present invention provides a process for the preparation of a pharmaceutically acceptable salt of lasofoxifene comprising reacting a pharmaceutically acceptable acid with lasofoxifene in solution.

Suitable pharmaceutically acceptable acids which can be used include, but are not limited to: inorganic acids such as phosphoric acid, hydrochloric acid, hydrobromic acid and organic acids such as acetic acid, tartaric acid, oxalic acid, methanesulfonic acid, paratoluenesulfonic acid and the like. Preferably the acid is tartaric acid.

Optionally, the acid is dissolved in a solvent before adding it to the solution of lasofoxifene free base.

The solvent used for the dissolution of lasofoxifene and the acid may be the same, or different solvents may be used.

Suitable solvents in which the acid addition salt of lasofoxifene can be prepared include but are not limited to include water, C1-C4 alcohols such as methanol ethanol, isopropanol, ketones such as acetone, methyl isobutyl ketone, 1,4-dioxane, aprotic solvents such as dimethyl formamide (DMF), dimethyl sulfoxide (DMSO), nitriles such as acetonitrile, ethers such as tetrahydrofuran and mixtures thereof.

The present invention provides a process for purification of lasofoxifene tartrate comprising:

a) providing a solution of lasofoxifene tartrate in a solvent or a mixture of solvents or their aqueous mixtures;
b) precipitating the solid from the solution, and
c) isolating lasofoxifene tartrate.

Suitable solvents in which purification of lasofoxifene tartrate can be carried out but are not limited are selected from C1-C4 alcohol, C1-C5 alcohol/water, C2-C5 nitrile, C2-C6 ether, a C2-C6 ester, a mixture of C2-C5 nitrile/C2-C6 ether, a mixture of C2-C6 ester/H2O, a mixture of C2-C6 ether/C3-C5 ketone, a mixture of C2-C6 ether/C2-C6 ester, a mixture of C2-C6 ether/C1-C5 alcohol, cyclic ether, hydrocarbon solvents and their halogenated derivatives, a C3-C5 carbonate, polar solvent such as dimethylformamide, dimethylsulfoxide, dimethyl acetamide and mixtures thereof, and mixtures of said organic solvents and water. Preferably acetonitrile, methyl tertiary butyl ether, methyl tertiary butyl methyl ether, tetrahydrofuran, methyl ethyl ketone, n-hexane and mixtures thereof, and mixtures of said organic solvents and water. The C2-C5 nitrile include acetonitrile, propionitrile and the like; C2-C6 ether include dimethyl ether, diethyl ether, isopropyl ether, methyl tertiary butyl ether (MTBE), methyl tertiary butyl methyl ether (MTBME); C2-C6 ester include ethyl acetate, isopropyl acetate, isobutyl acetate, t-butyl acetate and the like; C3-C5 ketone include acetone, methyl ethyl ketone, ethyl methyl ketone and the like; C1-C5 alcohol include methanol, ethanol, isopropanol, isobutanol, 2-butanol and the like; cyclic ether include tetrahydrofuran (THF), dioxane and the like; C3-C5 carbonate include dimethyl carbonate, diethyl carbonate and the like; hydrocarbon solvents and halogenated derivatives thereof may include pentane, n-hexane, heptane, cyclohexane, petroleum ether, m-, o-, or p-xylene, dichloromethane (MDC), chloroform, carbon tetrachloride, 1,2-dichloroethane and the like. More preferably purification is carried out in a solvent mixture of C1-C4 alcohol/water.

The present invention provides a process for purification of lasofoxifene tartrate by providing a solution of lasofoxifene tartrate in solvent selected C1-C4 alcohol such as ethanol, methanol; ether such as tetrahydrofuran; nitrile such as acetonitrile; combining the solution with an antisolvent such as water, diethylether, diisopropyl ether, acetone, hydrocarbons such as toluene, cyclohexane, n-hexane, maintaining the solution to obtain a precipitate and isolating purified lasofoxifene tartrate.

The present invention provides purified lasofoxifene tartrate comprising compound of formula IV less than 2%, preferably, less than 1%, preferably less than 0.1%.

Polymorphism is the occurrence of different crystalline forms of a single compound and it is a property of some compounds and complexes. Thus, polymorphs are distinct solids sharing the same molecular formula, yet each polymorph may have distinct physical properties. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry.

Figure 5:
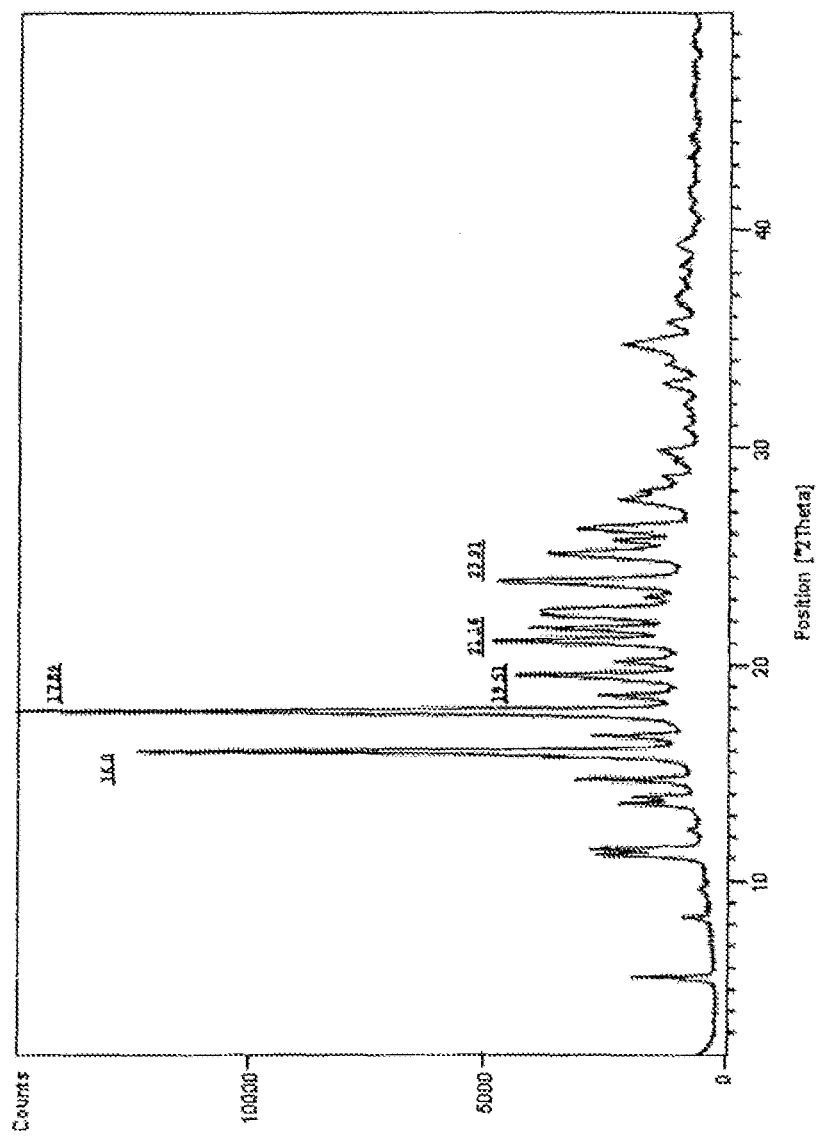
FIG. 5 represents XRD diffractogram of lasofoxifene tartrate obtained from example 10.
Figure 7:
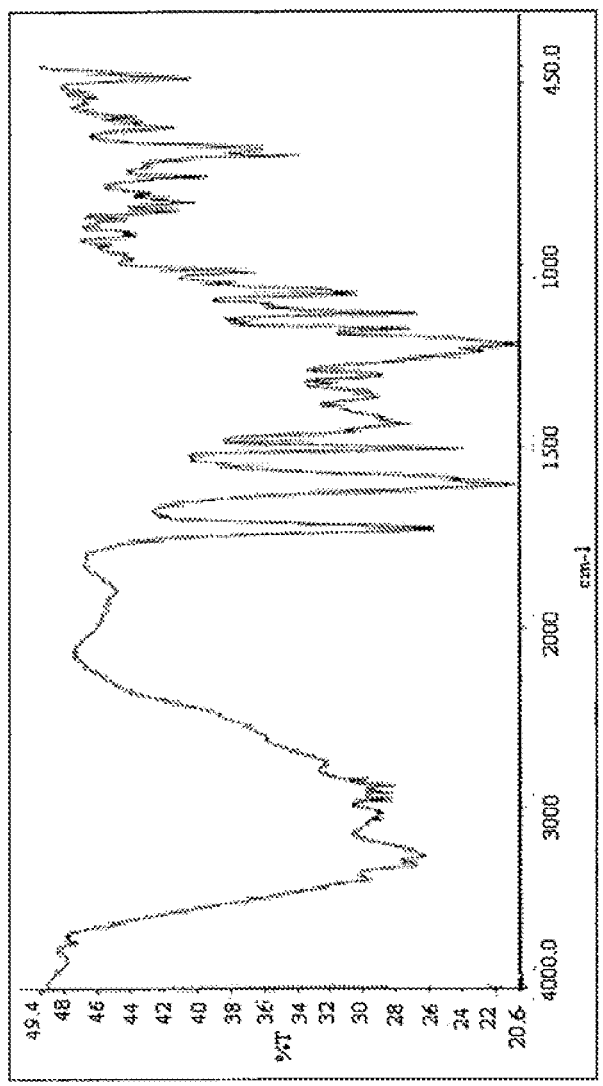
FIG. 7 represents IR spectra of lasofoxifene tartrate obtained from example 10

The present invention provides crystalline lasofoxifene tartrate characterized by an X-ray Diffraction (XRD) spectrum, which is substantially in accordance with FIG. 5, X-ray powder was performed on ARL X-ray diffractometer model XPERT-PRO (PANalytical) scanning parameters start position [° 2Th.] 2.01 and end position [° 2Th.] 49.98 and an Infrared (IR) spectrograph (KBr), which is substantially in accordance with FIG. 7.

Figure 6:
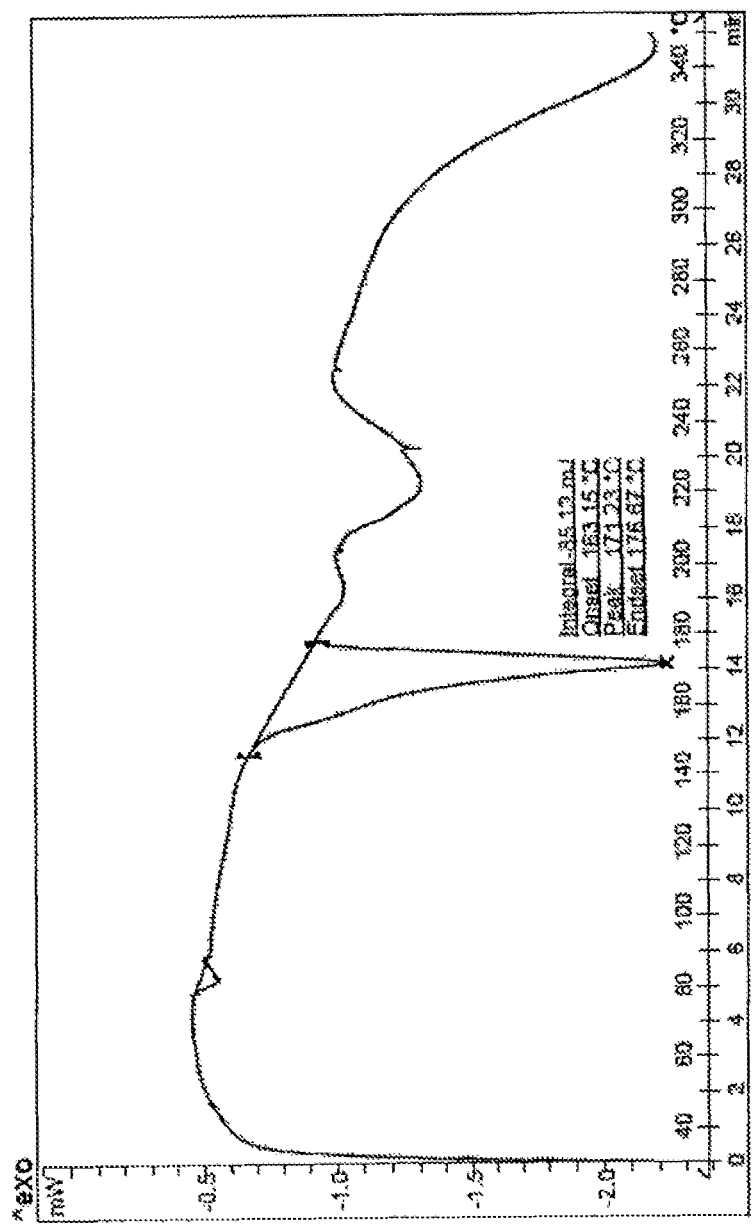
FIG. 6 represents DSC thermogram of lasofoxifene tartrate obtained from example 10.

The present invention provides crystalline lasofoxifene tartrate further characterized by a Differential Scanning calorimetric (DSC) thermogram with an endothermic curve at about 171.23° C. with an onset at about 163.15° C. and endset at about 176.67° C., which is substantially in accordance with FIG. 6, is measured by a Differential Scanning calorimeter (DSC 822, Mettler Toledo) at a scan rate of 10° C. per minute with an Indium standard.

Figure 8:
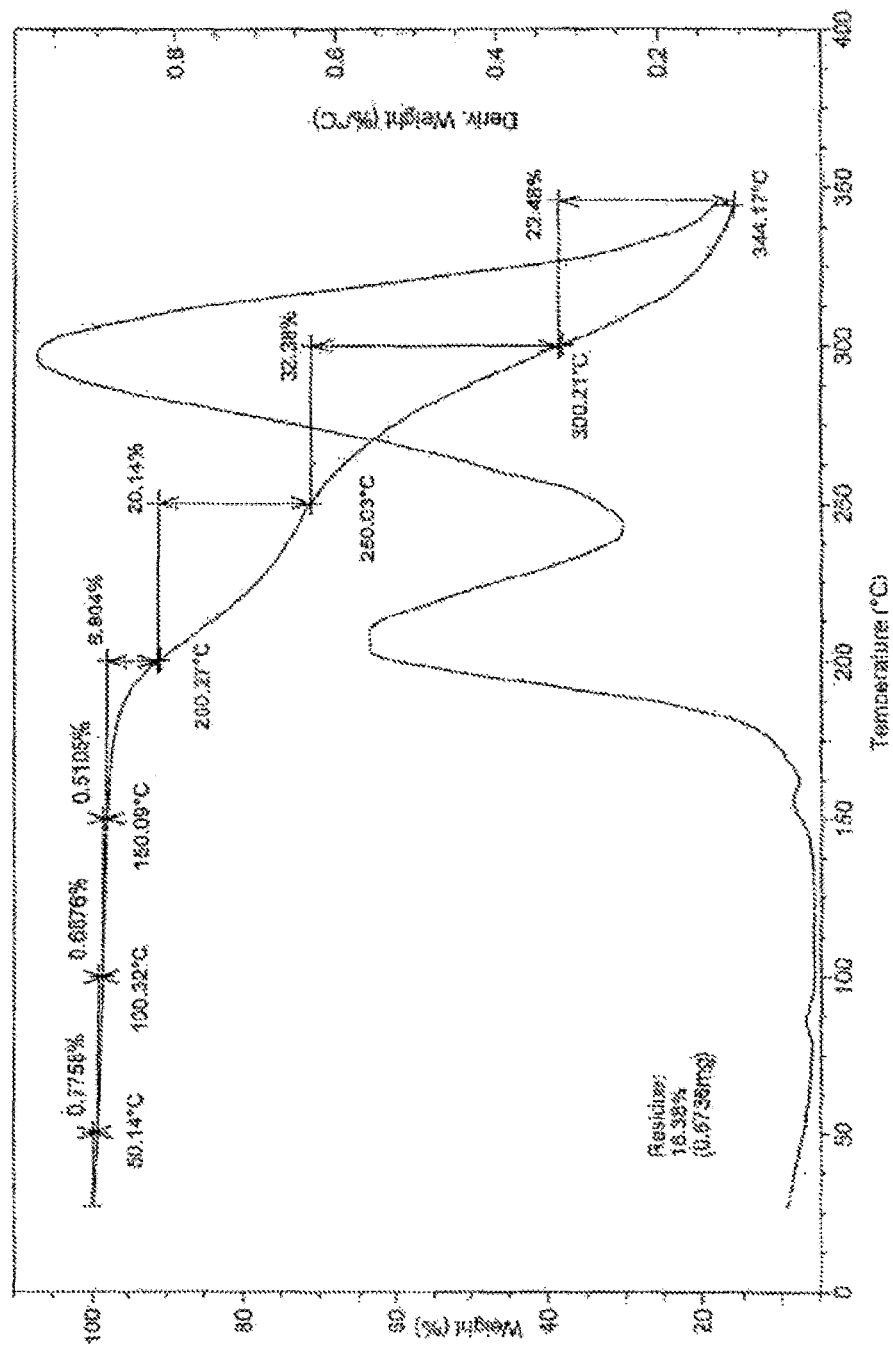
FIG. 8 represents TGA of lasofoxifene tartrate obtained from example 10

The present invention provides crystalline lasofoxifene tartrate further characterized by Thermogravimetric Analysis (TGA) thermogram showing a weight loss of about 0.6876% up to 100° C. determined over the temperature range of 30° C. to 350° C. and heating rate 10° C./min, which is substantially in accordance with FIG. 8.

The specific surface area of an active pharmaceutical ingredient may be affected by various factors. It is recognized that there is an inverse relationship between surface area and particle size; where the smaller the particle size, the higher the surface area. Whereupon, the available surface area for drug dissolution correlates to the rate of dissolution and solubility. A greater surface area enhances both the solubility and the rate of dissolution of a drug, which in turn, may improve its bioavailability and potentially its toxicity profiles.

Thus, there is a need in the art to prepare active pharmaceutical ingredients, such as lasofoxifene tartrate, with a high surface area to obtain formulations with greater bioavailability, and to compensate for any loss of surface area before formulation.

Specific surface area is defined in units of square meters per gram ($m^2/g$). It is usually measured by nitrogen absorption analysis. In this analysis, nitrogen is absorbed on the surface of the substance. The amount of the absorbed nitrogen (as measured during the absorption or the subsequent desorption process) is related to the surface area via a formula known as the BET formula.

The present invention further characterizes crystalline particles of lasofoxifene tartrate having a specific surface area from about 4 $m^2/g$ to about 7 $m^2/g$, as measured by Brunauer-Emmett-Teller (BET) method. Preferably, the surface area is 5.21 $m^2/g$.

In the field of pharmaceutical formulation, it is notable that particle size plays a pivotal role in the solubility properties of an API, like lasofoxifene tartrate. Particle size reduction techniques are commonly employed to increase a compound's solubility. Particle size reduction increases the surface area of the solid phase that is in contact with the liquid medium. However, particle size reduction cannot alter the solubility of the compound in a solvent, which is a thermodynamic quantity. At instances where the rate of dissolution of a poorly soluble drug is the rate limiting factor in its rate of absorption by the body, it is recognized that the bioavailability of such drugs may be enhanced when administration occurs in a finely divided state. Further, particle size can also affect how freely crystals or a powdered form of a drug will flow past each other, which in turn, has consequences in the production process of pharmaceutical products containing the drug.

In one aspect, the present invention provides crystalline lasofoxifene tartrate characterized by Malvern Mastersizer 2000® that demonstrates that the material comprises irregularly shaped particles with 90% of the particles having a particle size of less than 750 μm, 50% of the particles having a particle size of 250 μm and 10% of the particles having a particle size of 15 μm.

The particle size of lasofoxifene tartrate was measured under following Article I. conditions.

Instrument: Malvern Mastersizer
Sample Handling Unit: Hydro2000S (A)
Sample Preparation: Weigh accurately about 200-300 mg of well mixed sample in a beaker. Add 5-10 drops of dispersant. Make a uniform paste. Add 25 ml dispartant and stir to mix well. Disperse the sample in the dispersing media.
Material R.I.: 1.65
Material Absorption: 0.001
Dispersant Name: Liquid paraffin
Dispersant R.I.: 1.468
Model: General purpose
Sensitivity: Normal
Particle Shape: Irregular
Measurement Time: 12.0 secs
Background Time: 12.0 secs
Obscuration Range: 10-20%
Stirrer Speed: 2500 rpm
Ultrasonic: 60 sec, premeasurement
Tip displacement (sonication): 40%

Figure 9:
FIG. 9 represents SEM of lasofoxifene tartrate obtained from example 10

The present invention provides crystalline lasofoxifene tartrate having a flake morphology as observed by SEM, which is substantially in accordance with FIG. 9.

Tapped bulk density is defined as the maximum packing density of a powder (or blend of powders) achieved under the influence of well defined, externally applied forces. Thus factors include particle size distribution, true density, particle shape and cohesiveness due to surface forces including moisture affect the minimum packed volume. Flow properties and its compressibility can be predicted by tap density of the material and play a vital role in the overall tableting process, which requires that loose powders be compacted into a durable solid form with the correct mechanical strength, porosity and dissolution characteristics. These parameters are also important in the formation of oral suspensions, which ideally contain particles of high bulk density, enabling even dispersion of the particles throughout the suspension after shaking and before consumption.

In one aspect the present invention provides crystalline lasofoxifene tartrate having tapped bulk density ranging from about 0.26 g/ml to about 0.56 g ml and untapped bulk density ranging from about 0.22 g/ml to about 0.52 g/ml.

Preferably, the tapped density is 0.36 g/ml and the untapped density is 0.32 g/ml.

The present invention provides a lasofoxifene free base or a pharmaceutically acceptable salt thereof; preferably the tartrate salt obtained using the process of the described herein, may have a residual solvent content that is within the limits given by the International Conference on Harmonization of Technical Requirements for Registration of Pharmaceuticals for Human Use ("ICH") guidelines. The guideline solvent level depends on the type of solvent but is not more than about 5000 ppm, or about 4000 ppm, or about 3000 ppm.

The present invention provides lasofoxifene tartrate, obtained by the process disclosed herein, having less than about 1500 parts per million (ppm) $C_{1-4}$ alcohols such as methanol, ethanol, isopropanol, preferably less than about 1000 ppm; less than about 1000 ppm ethyl acetate, preferably less than about 500 ppm; less than about 1000 ppm tetrahydrofuran, preferably less than about 500 ppm; less than about 1000 ppm dichloromethane, preferably less than about 500 ppm.

While the present invention has been described in terms of its specific embodiments, certain modifications and equivalents will be apparent to those skilled in the art and are intended within the scope of the present invention.

The following examples are provided to enable one skilled in the art to practice the invention and are merely illustrative of the invention. The examples should not be read as limiting the scope of the invention as defined in the claims

EXAMPLE

Example 1

Preparation of 1-{2-[4-(6-Methoxy-3,4-dihydronaphthalene-1-yl)phenoxy]ethyl}pyrrolidine, Formula IV A solution of 140 g of 6-methoxy-1-tetralone in 400 ml of tetrahydrofuran (THF) was added to the Grignard reagent prepared from 200 g of 1-[2-(4-bromophenoxy)ethyl)]pyrrolidine and 23 g of Mg in 1000 ml of THF. The reaction mixture was stirred for 16 hours and then water (100 ml) was added. The reaction mass was filtered through Celite® and filtrate was concentrated. To the residue, water (1000 ml) was added and acidified with 2.5N HCl to bring the pH below 2. The acidic solution was extracted with diisopropyl ether (1000 ml). The aqueous layer was basified using 10% sodium hydroxide. The basic solution was extracted with methylene chloride (1000 ml) and was dried over anhydrous sodium sulphate. The methylene dichloride layer was concentrated. Residue obtained was taken up in diisopropyl ether (1000 ml) and stirred for 5 hours. The solid was filtered obtain the target product of 164 g of 1-{2-[4-(6-Methoxy-3,4-dihydronaphthalene-1-yl)phenoxy]ethyl}pyrrolidine, a compound of formula IV. Light brown color solid $^1$H NMR (400 MHz, CDCl$_3$): §7.26-7.23 (d, J=10.4 H/z, 2H), 6.96-6.90 (t, 3H), 6.76 (s, 1H), 6.64-6.62 (d, 11.2 Hz, 1H), 5.92-5.89 (t, 1H), 4.16-4.12 (t, 2H), 3.78 (s, 3H) 2.94-2.90 (t, 2H), 2.83-2.78 (t, 2H), 2.64 (s, 4H), 2.39-2.32 (m, 2H) 1.81 (s, 4H) m/z=350 (M+H):

m.p=71-75° C.

XRD Peaks: 9.13, 10.5, 15.78, 17.04, 18.06, 18.37, 19.01, 21.01, 21.13, 21.86, 22.87 and 23.43±0.2 °2Theta FT-IR (KBr): 554.9, 602, 622.7, 648, 674, 747.7, 790.8, 809.9, 817.1, 845.1, 879.7, 905.3, 953, 974, 1046, 1119.2, 1162.9, 1152, 1175.7, 1204.4, 1249.5, 1280.5, 1303, 1330, 1356.6, 1374.3, 1556, 1455.7, 1491.1, 1508.4, 1566.5, 1608.4, 1751.2 (br), 1881.5, 2080.4, 2773.4, 2809.9, 2920.4, 2940.5, 3031.9, 3444.4 cm$^{-1}$ DSC: Onset of 71.17° C.±2.0° C. and endset of 74.35° C.±2.0° C.

Example 2

Preparation of 1-{2-[4-(2-bromo-6-methoxy-3,4-dihydronaphthalene-1-yl)phenoxy]ethyl}pyrrolidine Formula V, To a solution of 1-{2-[4-(6-Methoxy-3,4-dihydronaphthalene-1-yl)phenoxy]ethyl}pyrrolidine 30 g (0.085 moles, 1 eq) in THF (750 ml) pyridinium bromide perbromide (30 g, 0.0937 moles, 1.1 eq) was added. The reaction mixture was stirred for 60 hours. The reaction mass was concentrated. The residue was dissolved in water (200 ml) and methylene chloride (200 ml). The biphasic layer was stirred for 1 hour at room temperature. Layers were separated and aqueous layer was washed with methylene chloride (2×120 ml). The organic layer was pooled and washed with 10% sodium hydroxide solution (1×120 ml) and washed with brine (100 ml). The organic layer was dried over anhydrous sodium sulphate and filtered. Filtrate was concentrated to obtain 32 g of 1-{2-[4-(2-bromo-6-methoxy-3,4-dihydronaphthalene-1-yl)phenoxy]ethyl}pyrrolidine oily product. HPLC purity: 98%.

Example 3

Preparation of 1-{2-[4-(6-Methoxy-2-phenyl-3,4-dihydronaphthalene-1-yl)phenoxy]ethyl}pyrrolidine hydrochloride (nafoxidene Hydrochloride) Formula VI Sodium carbonate (20.8 g, 0.196 moles, 2.8 eq) in water (150 ml) was added to a mixture of 1-{2-[4-(2-bromo-6-methoxy-3,4-dihydronaphthalene-1-yl)phenoxy] ethyl}pyrrolidine (30 g, 0.070 moles, 1 eq), phenylboronic acid (11.11 g, 0.091 moles, 1.3 eq) and tetrakis(triphenylphosphomum)palladium (2.77 g, 2.39 mmols, 0.034 eq) in THF 470 ml. The reaction was heated at reflux for 18 h. The layers were separated and the organic solution was washed with water followed by brine. The organic layer was dried over anhydrous sodium sulphate, filtered, and concentrated to yield 28.3 g of a brown solid. The solid was dissolved in a 1:1 mixture of methylene chloride and ethyl acetate (400 ml) and to this 1N HCl in diisopropyl ether (150 ml) was added. After stirring for 2 h, the crystals were filtered to obtain 20 g of 1-{2-[4-(6-Methoxy-2-phenyl-3,4-dihydronaphthalene-1-yl)phenoxy]ethyl}pyrrolidine hydrochloride (nafoxidene Hydrochloride materials. HPLC purity: 99%.

Example 4

Preparation of Cis-1-{2-[4-(6-Methoxy-2-phenyl-1,2,3,4-tetrahydronaphthalene-1-yl)phenoxy]ethyl}pyrrolidine Formula VII 1-{2-[4-(6-Methoxy-2-phenyl-3,4-dihydronaphthalene-1-yl)phenoxy]ethyl}pyrrolidene hydrochloride (nafoxidene Hydrochloride) (20 g, 0.0469 moles) was dissolved in 266 ml ethanol and 80 ml methanol. Wet Pd/C (5 g) was added and the mixture was hydrogenated on a Parr shaker at 50° C. and 150 psi for 10 hours. The catalyst was filtered off with the aid of celite and the solvents were evaporated under vacuum to yield Cis-1-{2-[4-(6-Methoxy-2-phenyl-1,2,3,4-tetrahydronaphthalene-1-yl)phenoxy]ethyl}pyrrolidene (10 g) off white foam HPLC purity: 95%.

Example 5

Preparation of Cis-6-5-[4-(2-pyrrolidin-1-yl-ethoxy)phenyl]-5,6,7,8-tetrahydronaphthalene-2-ol) Formula I A mixture of Cis-1-{2-[4-(6-Methoxy-2-phenyl-1,2,3,4-tetrahydronaphthalene-1-yl)phenoxy]ethyl)pyrrolidene 10 g was refluxed in 70 ml of 48% of aqueous hydrobromic acid in a nitrogen atmosphere for 5 hours. The reaction mixture was cooled and stirred for 16 h. To the reaction mass water (50 ml), MDC/Methanol (3:1) (56 ml) and 10% sodium bicarbonate solution (50 ml) was added. The reaction mixture was stirred to obtain a clear solution. Layers were separated and the organic layer was washed with methylene dichloride:methanol [(3:1) 2×50 ml] The combined organic layer was dried over anhydrous sodium sulphate, filtered and the filtrate was concentrated under vacuum to yield Cis-6-5-[4-(2-pyrrolidin-1-yl-ethoxy)phenyl]-5,6,7,8-tetrahydro-naphthalene-2-ol), off white foam 8 g. HPLC purity 95%.

Example 6

Preparation of (−) Cis-6-5-[4-(2-pyrrolidin-1-yl-ethoxy)phenyl]-5,6,7,8-tetrahydronaphthalene-2-ol D-tartarate A mixture of D-tartaric acid (16.4 g, 0.108 moles) in 160 ml ethanol and 22.5 ml water was heated to 50° C. to obtain a clear solution. To the above solution was added a solution of racemic Cis-6-5-[4-(2-pyrrolidin-1-yl-ethoxy)phenyl]-5,6,7,8-tetrahydronaphthalene-2-ol (45 g, 0.108 moles) in 290 ml of ethanol. The resulting solution was heated to mild reflux for 10 minutes. Reaction mixture was allowed to cool and was stirred at ambient temperature of about 25° C. for 20 hours. The crystals were filtered off and washed with ethanol (90 ml) to obtained (−) Cis-6-5-[4-(2-pyrrolidin-1-yl-ethoxy)phenyl]-5,6,7,8-tetrahydronaphthalene-2-ol D-tartarate. The product was dried at 50° C. for 6 hours at 760 mmHg vacuum. Yield: 22 g of lasofoxifene D-tartarate HPLC purity 95%.

Example 7

Purification of (−) Cis-6-5-[4-(2-pyrrolidin-1-yl-ethoxy)phenyl]-5,6,7,8-tetrahydronaphthalene-2-ol D-tartarate (−) Cis-6-5-[4-(2-pyrrolidin-1-yl-ethoxy)phenyl]-5,6,7,8-tetrahydronaphthalene-2-ol D-tartarate (2 g) was suspended in a mixture of tetrahydrofuran (THF) and ethanol (5 volume of solvent mixture, THF:ethanol (5:3)) and heated at reflux to obtain a clear solution. 3 volume of solvent mixture was distilled from the reaction mixture. The reaction mixture was stirred for 3 hour at 25° C.-30° C. The precipitate was filtered and dried to yield 1.2 g of pure lasofoxifene tartrate (HPLC purity 99.88%).

Example 8

Purification of (−) Cis-6-5-[4-(2-pyrrolidin-1-yl-ethoxy)phenyl]-5,6,7,8-tetrahydronaphthalene-2-ol D-tartarate (−) Cis-6-5-[4-(2-pyrrolidin-1-yl-ethoxy)phenyl]-5,6,7,8-tetrahydronaphthalene-2-ol D-tartarate (2 g) was suspended in a tetrahydrofuran (10 volume) and heated at reflux to obtain a clear solution. 3 volume of the solvent was distilled under vacuum. The reaction mixture was stirred at 20° C.-25° C. for 3 hour. The precipitate was filtered and dried to yield 1.1 g of pure lasofoxifene tartrate (HPLC purity 99.65%).

Example 9

Purification of (−) Cis-6-5-[4-(2-pyrrolidin-1-yl-ethoxy)phenyl]-5,6,7,8-tetrahydronaphthalene-2-ol D-tartarate (−) Cis-6-5-[4-(2-pyrrolidin-1-yl-ethoxy)phenyl]-5,6,7,8-tetrahydronaphthalene-2-ol D-tartarate (2 g) was suspended in a methanol (5 volume) and heated at reflux to obtain a clear solution. 2 volume of the solvent was distilled under vacuum. The reaction mixture was cooled to 0-5° C. The reaction mixture was stirred for 3 hours at 0-5° C. The precipitate was filtered off and washed with chilled methanol (1 v) to yield 1.35 g of pure lasofoxifene tartrate (HPLC 99.84%).

Example 10

Purification of (−) Cis-6-5-[4-(2-pyrrolidin-1-yl-ethoxy)phenyl]-5,6,7,8-tetrahydronaphthalene-2-ol D-tartarate (−) Cis-6-5-[4-(2-pyrrolidin-1-yl-ethoxy)phenyl]-5,6,7,8-tetrahydronaphthalene-2-ol D-tartarate (2 g) was suspended in a mixture of ethanol and water (7 volume of solvent mixture ethanol:water (95:5)) and heated at reflux to obtain a clear solution. 4 volume of the solvent mixture was distilled. The reaction mixture was stirred at 25-30° C. for 4 hours and the precipitate was filtered and washed with 2 v ethanol to yield 1.3 g of pure lasofoxifene tartrate. (HPLC purity 99.9%, Chiral purity: 99.9% ee; compound of formula IV<0.1%)

Example 11

Purification of (−) Cis-6-5-[4-(2-pyrrolidin-1-yl-ethoxy)phenyl]-5,6,7,8-tetrahydronaphthalene-2-ol D-tartarate (−) Cis-6-5-[4-(2-pyrrolidin-1-yl-ethoxy)phenyl]-5,6,7,8-tetrahydronaphthalene-2-ol D-tartarate (1.5 g) was suspended in a acetonitrile (5 volume) and heated at reflux to obtain a clear solution. Two volume of the solvent was distilled under vacuum and reaction mixture was allowed to cool to a temperature of about 5° C. to 10° C. The reaction mixture was stirred for 4 hours at 5° C.-10° C. and the precipitate was filtered and washed with 1 v chilled acetonitrile to yield (0.6 g) pure lasofoxifene tartrate (HPLC purity 99.80%).

Example 12

Purification of (−) Cis-6-5-[4-(2-pyrrolidin-1-yl-ethoxy)phenyl]-5,6,7,8-tetrahydronaphthalene-2-ol D-tartarate (−) Cis-6-5-[4-(2-pyrrolidin-1-yl-ethoxy)phenyl]-5,6,7,8-tetrahydronaphthalene-2-ol D-tartarate (2.2 g) was suspended in a acetonitrile (5 volume) and heated at reflux to obtain a clear solution. To this solution water (3 v) was added and stirred for 30 minutes. The precipitate was filtered and washed with acetonitrile water (2 v) mixture (5:3 ratios) at 25° C.-30° C. and then dried to yield 1.4 g of pure lasofoxifene tartrate. (HPLC purity 99.87%)

The crystalline lasofoxifene tartrate can also be purified as follows:
(i) (−) Cis-6-5-[4-(2-pyrrolidin-1-yl-ethoxy)phenyl]-5,6,7,8-tetrahydronaphthalene-2-ol D-tartarate is suspended in diethyl ether or diisopropyl ether (10 volume);
(ii) heated to reflux to obtain a clear solution;
(iii) cooled and filtered the slurry.

The invention claimed is:
1. A solid crystalline form of 1-(2-[4-(6-methoxy-3,4-dihydronaphthalene-1-yl)phenoxy]ethyl)pyrrolidine, compound of formula IV,

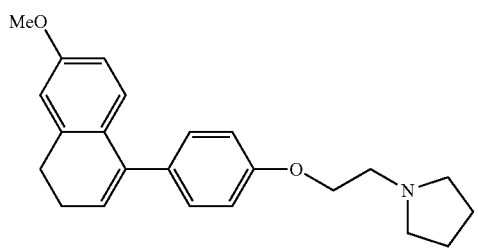

Formula IV characterized by XRD peaks at 9.13, 17.04, 18.37, 19.01 and 22.87±0.2 °2 theta and DSC onset of 71.17° C.±2.0° C. and endset of 74.35° C.±2.0° C.

2. A process for the preparation of a solid crystalline form of 1-(2-[4-(6-methoxy-3,4-dihydronaphthalene-1-yl)phenoxy]ethyl)pyrrolidine of claim 1 comprising reacting 6-methoxy-1-tetralone with a Grignard reagent of 1-[2-(4-bromophenoxy)ethyl)]pyrrolidine, a compound of formula III,

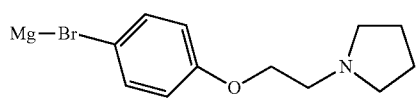

Formula III in the presence of a solvent.

3. The process of claim 2, wherein the solvent is an ether solvent.

4. The process of claim 2, wherein the reaction temperature is between about 0° C. to about reflux temperature of the solvent.

5. The process of claim 3 wherein the reaction temperature is between about 20° C. to about 30° C.

6. A process for the preparation of Cis-6-phenyl-5-[4-(2-pyrrolidin-1-yl-ethoxy)phenyl]-5,6,7,8-tetrahydronaphthalene-2-ol, a compound of formula I,

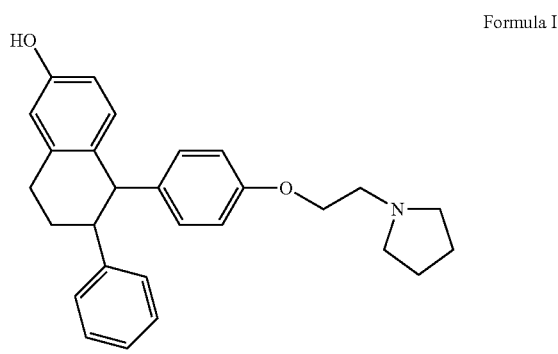 [SMILES: Oc1ccc2c(c1)CCC(c1ccccc1)C2c1ccc(OCCN2CCCC2)cc1]

Formula I comprising:
a) halogenating a solid compound of formula IV of claim 1,

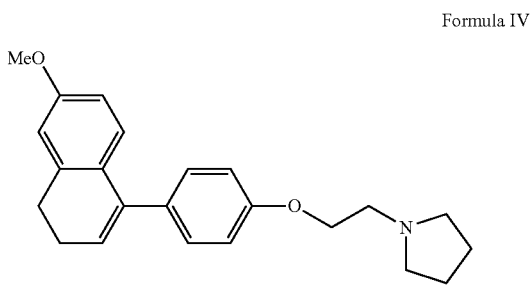 [SMILES: COc1ccc2c(c1)CCC=C2c1ccc(OCCN2CCCC2)cc1]

Formula IV to obtain a compound of formula V,

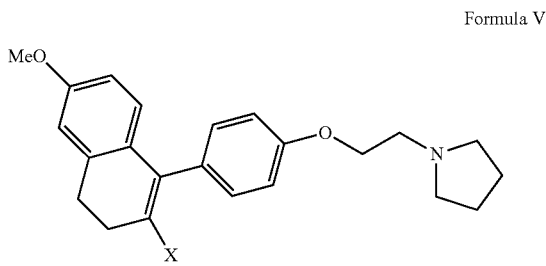

Formula V where X is a halogen selected from chlorine, bromine, or iodine;
b) phenylating the compound of formula V to obtain 1-(2-[4-(6-methoxy-2-phenyl-3,4-dihydronaphthalene-1-yl)phenoxy]ethyl)pyrrolidine hydrochloride, a compound of formula VI, Formula VI

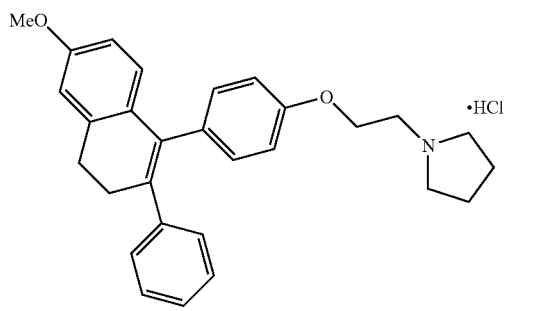

wherein the phenylating agent is selected from the group consisting of phenyl boronic acid, phenyl boronic acid glycol ester, and phenyl boron di-halogen;
c) reducing the compound of formula VI to obtain cis-1-(2-[4-(6-methoxy-2-phenyl-1,2,3,4-tetrahydronaphthalene-1-yl)phenoxy]ethyl)pyrrolidine, a compound of formula VII, Formula VII

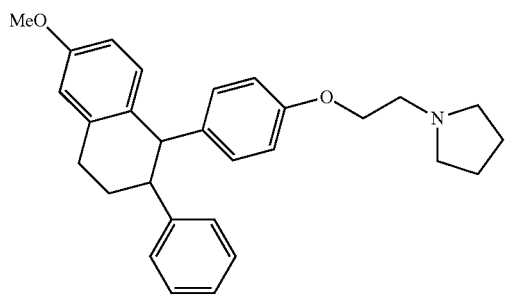

wherein the reducing agent is selected from the group consisting of palladium/C (5-20%), palladium hydroxide, Raney Nickel or activated alloy catalyst,
d) reacting the compound of formula VII with an acid to obtain a compound of formula I Formula I

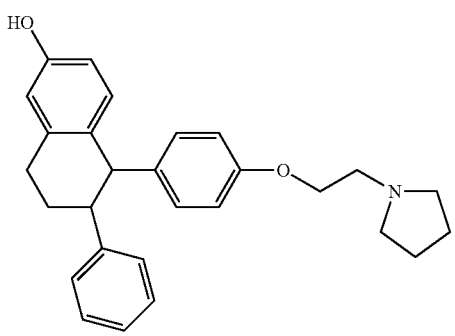

wherein the acid is selected from the group consisting of 48% hydrobromic acid, hydroiodic acid, acetic acid in hydrobromic acid and boron tribromide in methylene chloride;
e) Optionally converting the compound of formula I to its corresponding pharmaceutically acceptable salt/s.

7. A process for purification of lasofoxifene tartrate of claim 6 comprising:
a) providing a solution of lasofoxifene tartrate in a solvent or a mixture of solvents or their aqueous mixtures;
b) precipitating the solid from the solution, and
c) isolating lasofoxifene tartrate.

8. The process of claim 7, wherein the solvent is selected from the group consisting of acetonitrile, tetrahydrofuran, dimethylsulfoxide, methanol, ethanol mixtures thereof, and mixtures of said solvents and water.

9. A crystalline lasofoxifene tartrate characterized by an X-ray Diffraction (XRD) spectrum, characterized by XRD peaks at 16.0, 17.89, 19.51, 21.16, 23.91±0.2 °2 theta which is substantially in accordance with FIG. 5; and a Differential Scanning Calorimetric (DSC) thermogram, with an endothermic curve at about 171.23° C. with an onset at about 163.15° C. and endset at about 176.67° C., which is substantially in accordance with FIG. 6.

10. The crystalline lasofoxifene tartrate of claim 9 having characteristic Infrared (IR) spectrograph, which is substantially in accordance with FIG. 7; and a Thermogravimetric Analysis (TGA) thermogram, showing a weight loss of about 0.6876% up to 100° C. which is substantially in accordance with FIG. 8.

11. The crystalline lasofoxifene tartrate of claim 9, which are particles having a specific surface area from about 4 m²/g to about 7 m²/g, as measured by Brunauer-Emmett-Teller (BET) method.

12. The crystalline lasofoxifene tartrateof claim 9 which are particles, wherein 90% of the particles have a particle size less than 750 µm.

13. The crystalline lasofoxifene tartrate of claim 9 having flake morphology as observed by SEM, which is substantially in accordance with FIG. 9.

14. The crystalline lasofoxifene tartrate of claim 9 having a tapped bulk density ranging from about 0.26 g/ml to about 0.56 g/ml and untapped bulk density of about 0.22 g/ml to about 0.52 g/ml.

15. The process of claim 3, wherein the ether solvent is selected from the group consisting of tetrahydrofuran, diisoprpyl ether and diethyl ether.

16. The process of claim 6, wherein the phenylating agent of step (b) is a phenyl boron di-halogen selected from the group consisting of phenyl boron dichloride, phenyl boron dibromide and phenyl boron diiodide.

* * * * *